United States Patent [19]
Jacobsen et al.

[11] Patent Number: 6,086,562
[45] Date of Patent: Jul. 11, 2000

[54] DISPOSABLE AUTOMATIC INJECTION DEVICE

[75] Inventors: Stephen C. Jacobsen, Salt Lake City; Aaron M. Best, West Jordan; Tomasz J. Petelenz, Salt Lake City, all of Utah

[73] Assignee: Sarcos, Inc., Salt Lake City, Utah

[21] Appl. No.: 09/165,164

[22] Filed: Oct. 1, 1998

Related U.S. Application Data

[63] Continuation-in-part of application No. 08/797,295, Feb. 7, 1997, Pat. No. 5,860,957.

[51] Int. Cl.$^7$ .................................................. A61M 05/20
[52] U.S. Cl. ............................ 604/156; 604/131; 604/19
[58] Field of Search .................................. 604/19, 22, 46, 604/47, 48, 51, 52, 69, 73, 130, 131, 132, 140, 141, 143–147, 156, 246, 257, 264, 272; 606/1, 167, 185; 600/573, 576

[56] References Cited

U.S. PATENT DOCUMENTS

| | | |
|---|---|---|
| 3,840,009 | 10/1974 | Michaels et al. . |
| 4,102,332 | 7/1978 | Gessman . |
| 4,141,359 | 2/1979 | Jacobsen et al. . |
| 4,250,878 | 2/1981 | Jacobsen et al. . |
| 4,312,347 | 1/1982 | Morgoon et al. . |
| 4,326,522 | 4/1982 | Guerrero et al. . |
| 4,425,117 | 1/1984 | Hugemann et al. . |
| 4,439,197 | 3/1984 | Honda et al. . |
| 4,457,752 | 7/1984 | Vadasz . |
| 4,552,554 | 11/1985 | Gould et al. . |
| 4,564,363 | 1/1986 | Bagnall et al. . |
| 4,886,499 | 12/1989 | Cirelli et al. ............................ 604/131 |
| 4,968,297 | 11/1990 | Jacobsen et al. . |
| 5,116,305 | 5/1992 | Milder et al. . |
| 5,135,479 | 8/1992 | Sibalis et al. . |
| 5,167,625 | 12/1992 | Jacobsen et al. . |
| 5,196,002 | 3/1993 | Hanover et al. . |
| 5,413,581 | 5/1995 | Goy . |
| 5,464,395 | 11/1995 | Faxon et al. . |
| 5,522,798 | 6/1996 | Johnson et al. . |
| 5,527,288 | 6/1996 | Gross et al. ............................ 604/140 |
| 5,582,593 | 12/1996 | Hultman . |
| 5,616,132 | 4/1997 | Newman ................................ 604/140 |
| 5,860,957 | 1/1999 | Jacobsen et al. ...................... 604/140 |

*Primary Examiner*—Glenn K. Dawson
*Attorney, Agent, or Firm*—Thorpe, North & Western

[57] ABSTRACT

An automatic injection device includes a drug-filled vessel having a flexible membrane over a first opening thereof and a puncturable seal in a wall thereof, a hollow needle attached at a first end to the flexible membrane and having a sharp end positioned proximate the puncturable seal housing. A pressure source such as a combustible propellant provides a compressed gas above the flexible membrane to force the membrane into the drug-filled vessel, forcing the hollow needle through the puncturable seal and the drug contained in the vessel through the hollow needle. After the drug has been substantially evacuated from the vessel, the membrane is allowed to return to its pre-expanded state thus retracting the hollow needle into the vessel. Preferably, the flexible membrane is an elastomeric material having a plurality of concentrically configured corrugations to allow expansion of the membrane into the vessel. The inner surface of the vessel may have a dome-like shape such that expansion of the membrane into the vessel substantially matches the dome-like shape and thus forces substantially the entire amount of the drug from the vessel.

28 Claims, 4 Drawing Sheets

DISPOSABLE AUTOMATIC INJECTION DEVICE

This application is a continuation-in-part of U.S. patent application Ser. No. 08/797,295 filed Feb. 7, 1997 now U.S. Pat. No. 5,860,957.

BACKGROUND

1. Field of the Invention

The present invention generally relates to an apparatus for injecting drugs into a patient and, more specifically, to an automatic injection device that utilizes a flexible membrane assembly and a propellant to automatically inject a single dose of a drug into a patient when the propellant is ignited.

2. Background of the Invention

Presently available automatic injection systems are typically large and bulky devices requiring skill and training in order to properly operate the device. Accordingly, such devices are not amenable to applications for which rapid administration of either a single drug or a combination of different compounds in rapid succession is desirable. Such systems are commonly used for mass vaccinations and self-administration of medications—such as for injection of insulin in diabetic patients, epinephrine in anaphylactic shock, and antimigraine drugs (e.g., sumatriptan). Devices for self-administration typically require cleaning after each use. Automated injectors used for mass vaccinations, as in military applications, typically use the same injection head for all patients and often require a supply of compressed gas.

Automatic injection devices are also presently in use for parenteral administration of medications under field conditions, where injections with a syringe are either impractical, require undue attention or training, or are painful. Examples of such situation s are administration of chemical warfare antidotes (e.g., atropine) and treatment of anaphylactic shock (e.g., epinephrine). In both instances, drug administration must be rapid, simple and reliable and must minimize the possibility of human error on selection and administration of drug doses. One such automatic injection device used by the military comprises an elongate tube with a needle protruding from one end. The needle is rapidly and forcefully inserted into a muscle, resulting in the painful injection of a drug contained within the tube. Upon removal of the needle, however, the needle remains exposed and thus requires proper handling to prevent contact by and/or injury to other persons.

For mass vaccination programs, reduction of the delivery costs associated with immunizations presents a big opportunity to boost immunization coverage rates. One way to decrease costs is to reduce the number of trained personnel required to complete an immunization series. Frequently, patient compliance is a major factor limiting effectiveness of mass vaccination programs—children, parents, and health care providers are less willing to accept the increased numbers of separate injections. Thus, it is desirable to deliver as many vaccines as possible during a single, quick patient visit. Mixing of vaccines in one syringe is often contraindicated due to potential incompatibilities and a reduced potency of the mixed vaccines. However, vaccines are typically safe and effective when administered at the same time at different application sites, such as with a single, multiple-site injection. Therefore, there is a clear need to simultaneously inject several vaccines into a patient with each vaccine being delivered at a discrete injection site. Due to problems associated with typical needle injections, including transmission of disease between patients, hazards to health-care workers, and expensive handling and disposal procedures, a method and apparatus for injecting a patient without using needles or by utilizing retractable needles is desirable.

U.S. Pat. No. 5,167,625 to Jacobsen et al. discloses an implantable drug delivery system which includes a housing having a plurality of compartments, each of which includes a flexible drug containment sack. A cover is disposed over the compartment openings to prevent the inadvertent release of drug formulations contained in the sacks. Gas generating elements are disposed in the compartments and are responsive to an initiation signal for producing gas to force the sacks and drug formulations out of the housing. Such a device, however, is designed for internal use, requiring surgery for implantation.

A portable, hand-held injection device is disclosed in U.S. Pat. No. 5,616,132 to Newman, and includes a diaphragm mounted within a housing having a needle associated therewith that moves in response to movement of the diaphragm when pressurized gas is released into the housing. Each device, however, is a completely self-contained unit that would be relatively expensive to manufacture, and difficult, if not impossible, to reuse. Accordingly, such a device would be impractical for mass injection scenarios as previously discussed.

Thus, it would be advantageous to provide prefilled, interchangeable and disposable injection devices that are inexpensive, easy to use, and safe for both the patient and medical personnel. It would also be advantageous to provide a prefilled injection device that reduces the risk associated with cross-infection, improves compliance—especially in children—improves the effectiveness of vaccination programs, does not require special sharps handling for disposal, and is a self-contained unit that presents a single item with few contaminated components for disposal.

SUMMARY OF THE INVENTION

It is an object of the present invention to provide an automatic injection device that eliminates the need for special handling and disposal of contaminated needles.

It is another object of the present invention to provide an automatic injection device that is disposable.

It is yet another object of the present invention to provide an automatic injection device that is easy to use by a person without medical training and minimizes human error associated with the administration of drugs.

It is an object of the present invention to provide an automatic injection device that quickly administers the drug.

It is an object of the present invention to provide an automatic injection device that is compact.

It is an object of the present invention to provide an automatic injection device that is simple to manufacture.

It is an object of the present invention to provide an automatic injection device that reliably delivers a substantially precise dose of a drug.

Accordingly, an apparatus for administering a single dose of a drug in liquid form comprises a drug-filled vessel defined by a substantially rigid container and a flexible membrane. The membrane when stretched is preferably capable of expanding into the container such that the membrane displaces any drug disposed within the container. A hollow needle is disposed substantially within the vessel being attached at a proximal end to the membrane. The needle includes one or more openings along the length thereof, preferably at least one proximate its proximal end.

In addition, the needle includes an opening at its distal end, the distal end providing a sharpened tip. The sharpened tip of the needle is preferably positioned proximate to a puncturable seal provided in the wall of the container. A pressure source, such as a compressed gas or combustible propellant, is provided adjacent to the membrane on the opposite side from the drug within the vessel.

When activated, pressure from the pressure source expands or forces the membrane into the container. Substantially simultaneously, the sharpened tip of the needle pierces the puncturable seal and protrudes therethrough. When the opening at the distal end of the needle protrudes through the puncturable seal, the drug contained within the vessel is allowed to flow into the one or more openings along the length of the needle and out the opening at the distal end. After the drug has been sufficiently evacuated from the vessel, the membrane is allowed to return to its unstressed state, thus retracting the needle back into the vessel.

Preferably, the membrane is comprised of a resilient material configured in one or more concentric corrugations, with the needle attached proximate the center of the membrane. In addition, it is also preferable that the container has a dome-like shape with the membrane covering the open end of the dome. Thus, when the membrane expands into the container, the membrane substantially contacts a substantial portion of the inner surface of the container. As such, a substantial portion of the drug contained in the vessel is forced from the container through the needle. Accordingly, little of the drug is wasted and a substantially precise dose of the drug can be reliably administered.

In order to create a desired amount of pressure above the membrane, it is preferable that a pressure chamber be defined by a cap that is positioned above the membrane and forms a seal therewith. If a propellant is employed to pressurize the pressure chamber, gases generated from the combustion fill the pressure chamber and force the membrane into the container.

The pressure source preferably comprises a highly combustible material, such as a propellant that forms a gas when ignited, and an igniter to ignite the combustible material. The igniter is preferably a circuit that utilizes an electrical source, such as a battery, to heat a fusible link, such as a resistor, a resistor screen printed onto a circuit board, NiCr wire, or tungsten wire, to a temperature at which the propellant ignites and activates the device. A valve or vent is also preferably provided in the device so that gas generated by the combustion of propellant can be vented to allow the membrane or piston to retract back into the housing. Such a valve may be mechanical or may be filled with a meltable material, or a wax or polymeride plug, that can be opened after the drug has been injected to vent the device and allow the needle, if any, to retract back into the device.

In order to more fully understand the manner in which the above-recited objects and advantages of the invention are obtained, a more particular description of the invention will be rendered by reference to the presently preferred embodiments or presently understood best mode thereof that are illustrated in the appended drawings.

BRIEF DESCRIPTION OF THE DRAWINGS

The embodiments illustrated in the following drawings are provided by way of example of the preferred embodiments of the invention and are therefore not to be considered as limiting the scope of the present invention, in which.

DETAILED DESCRIPTION OF THE PREFERRED EMBODIMENTS

Figure 1A:
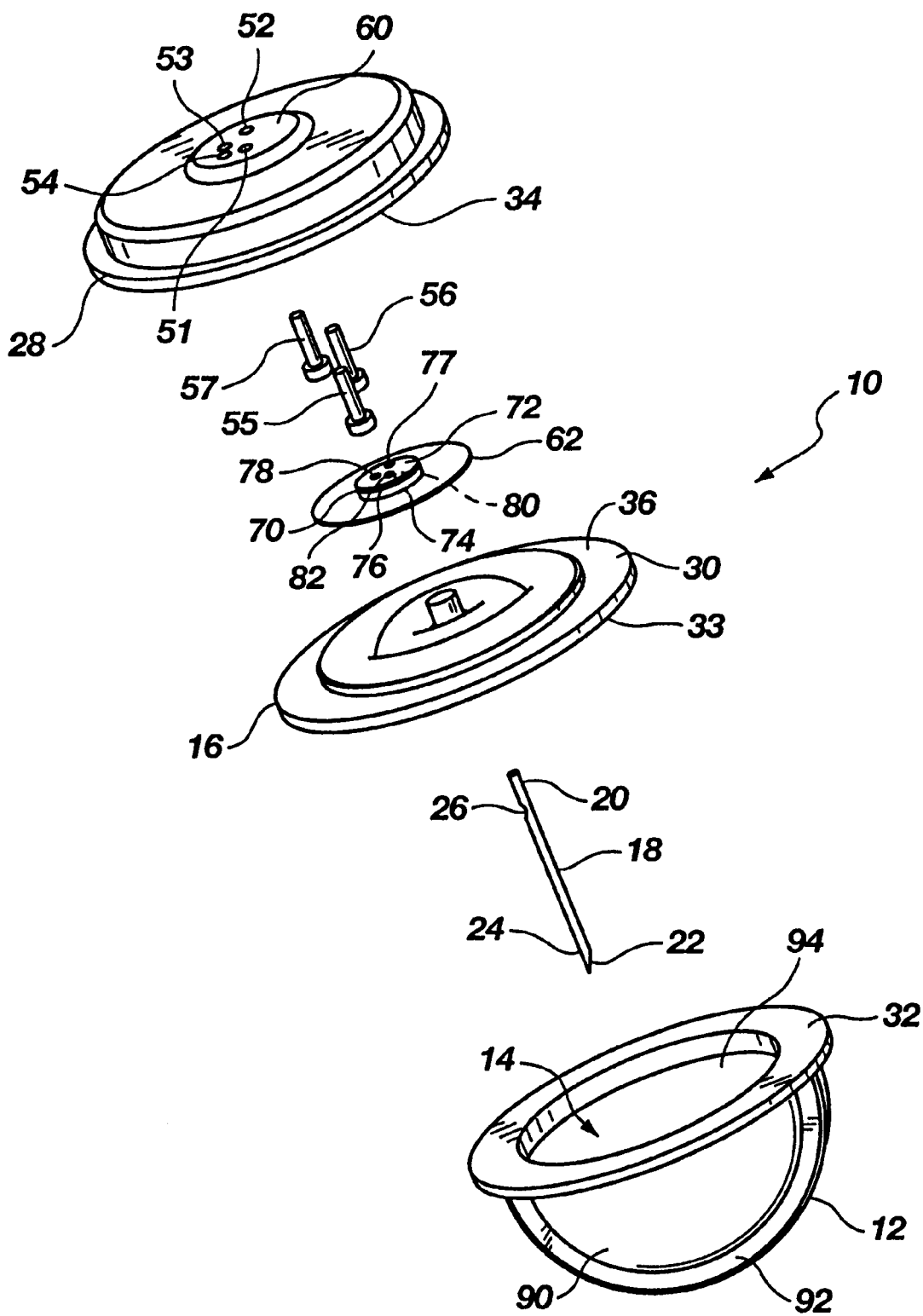
FIG. 1A is an exploded perspective view of a preferred embodiment of an automatic injection device in accordance with the present invention.

FIG. 1A illustrates an exploded perspective view of an automatic injection device, generally indicated at 10, according to the present invention, comprising a housing or vessel 12 having a generally dome-like shape, preferably formed from polyurethane or other materials known in the art. It is also contemplated that other shapes of the vessel 12 may also be employed. The vessel 12 defines an interior chamber 14 or drug reservoir for containing a dose of a drug. The rest of the components of the automatic injection device 10 are generally fitted within or onto the vessel 12 and include a flexible expulsion means such as a diaphragm or membrane 16 of generally disk-like configuration, preferably comprised of an elastomeric material such as a soft diameter, flexible polyurethane, silicone rubber or latex rubber, or some other substantially flexible and/or resilient material known in the art. The membrane 16 together with the vessel 12 define a sealed drug capsule or container for containing a drug therein. A hollow needle 18, preferably comprised of stainless steel or some other material known in the art, or some other ejection means, such as a nozzle, is positioned within the vessel and is secured by its proximal end 20 to the membrane 16. The needle 18 is provided with a first opening 22 at its distal end 24 for delivery of the drug from the vessel 12. A second opening 26 is provided along the length of the needle 16 proximate the proximal end 20 to allow the drug contained within the vessel to flow through the second opening 26 and out the first opening 22 when the distal end of the needle 16 is outside of the vessel 12.

The membrane 16 is provided with an outer flange 30 that extends around the perimeter of the membrane 16. In addition, the vessel 12 is provided with a first circumferential mating surface 32 configured to abut against a first side 33 the flange 30 when the vessel 12 and membrane 16 are brought into contact. A rear housing 28 of generally cylindrical configuration is provided with a second circumferential mating surface 34 configured to abut against a second side 36 of the flange 16. Thus, the vessel 12 and rear housing 28 effectively sandwich the membrane 16 thereinbetween, forming a substantially fluid tight seal between the vessel 12 and the membrane 16 and between the membrane 16 and the rear housing.

Figure 1B:
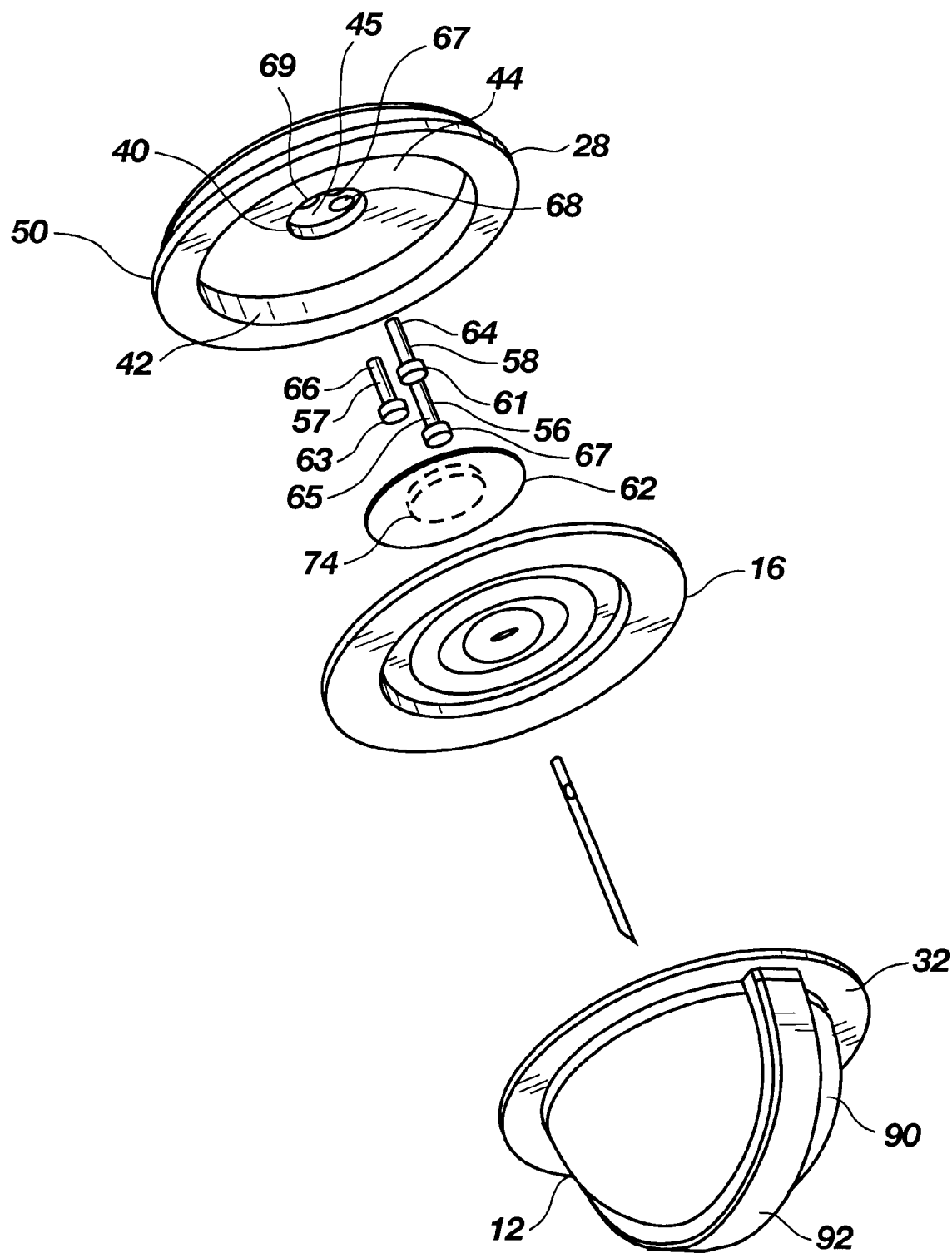
FIG. 1B is an exploded perspective view of the automatic injection device illustrated in FIG. 1A.

As further illustrated in FIG. 1B, the rear housing 28 defines a first opening 45 in an interior surface 44 thereof and a chamber 42. When the rear housing 28 is mated with the membrane 16, the membrane 16 and chamber 42 form an air- or liquid-tight seal and define a pressure chamber thereinbetween. In this preferred embodiment, the first opening 45 is provided for housing a quantity of a propellant 74, so that when the propellant is ignited, the gas generated from the combustion of the propellant expands into the pressure chamber forcing the membrane 16 into the vessel 12.

Referring again to FIG. 1A, a plurality of holes 51–54 are provided in the rear housing 50. Three of the holes 51–53 are configured for receiving connector pins 55–57 which provide an electrical contact to the igniter circuitry (not shown). It is also contemplated that other means of providing an electrical connection between igniter and the electrical controller may also be employed. Thus, when assembled, the shafts 64–66 (see FIG. 1B) of the connector pins 55–57, respectively, fit into the holes 51–53 and protrude a distance above the top surface 60 of the rear housing 28. In addition, as shown in FIG. 1B, the heads 61, 63, and 67 of the connector pins 55–57 fit into receptacles or larger recesses 67–69 formed at the end of each hole 51–53 at the surface 45. Thus, the heads 61–63 fit substantially flush with the surface 45 when fitted into the recesses 67–69, respectively. As further shown in FIG. 1A, a disk-shaped foil cover 62 may be provided to fit against the interior surface 44 (see FIG. 1B) of the rear housing 50 and protect the membrane 16 from being damaged by heat during the propellant combustion process.

A propellant and igniter assembly 70 is preferably preformed and sized to fit within the recess 40 defined by the surface 44 (see FIG. 1B). The igniter assembly 70 is essentially comprised of a small disc-shaped printed circuit board, or some other structure to which electrical components may be attached, in contact with a quantity of propellant 74. It is noted that while the propellant 74 is shown in a disk-like form, it may actually be screen printed, drop-shape (deposited from a solution) or may be comprised of loose particles that are held in the recess 40 with the foil sheet 62. The igniter 72 preferably includes a fusible link 80 connected between the contact pads 76 and 77 on the side of the circuit board adjacent the propellant 74. The propellant 74 is preferably deposited on or around and in close contact with the igniter 72 (fusible link). The fusible link 80 may be comprised of a NiCr or tungsten wire, a screen printed resistor, or some other device known in the art that will generate sufficient heat when an electrical current is passed therethrough to ignite the propellant. A second fusible link 82 is preferably in contact with the contact pads 76 and 78 and is positioned on the top side of the circuit board 72. The second fusible link 82 is preferably positioned to be in contact with the vent hole 54.

As further illustrated in FIGS. 1A and 1B, the vessel 12 is comprised of a dome-shaped cap 90 circumscribed by an elongate cap puncture member 92. The circumferential mating surface or flange 32 is secured to or formed integrally with the rim or perimeter of the opening 94.

Figure 2:
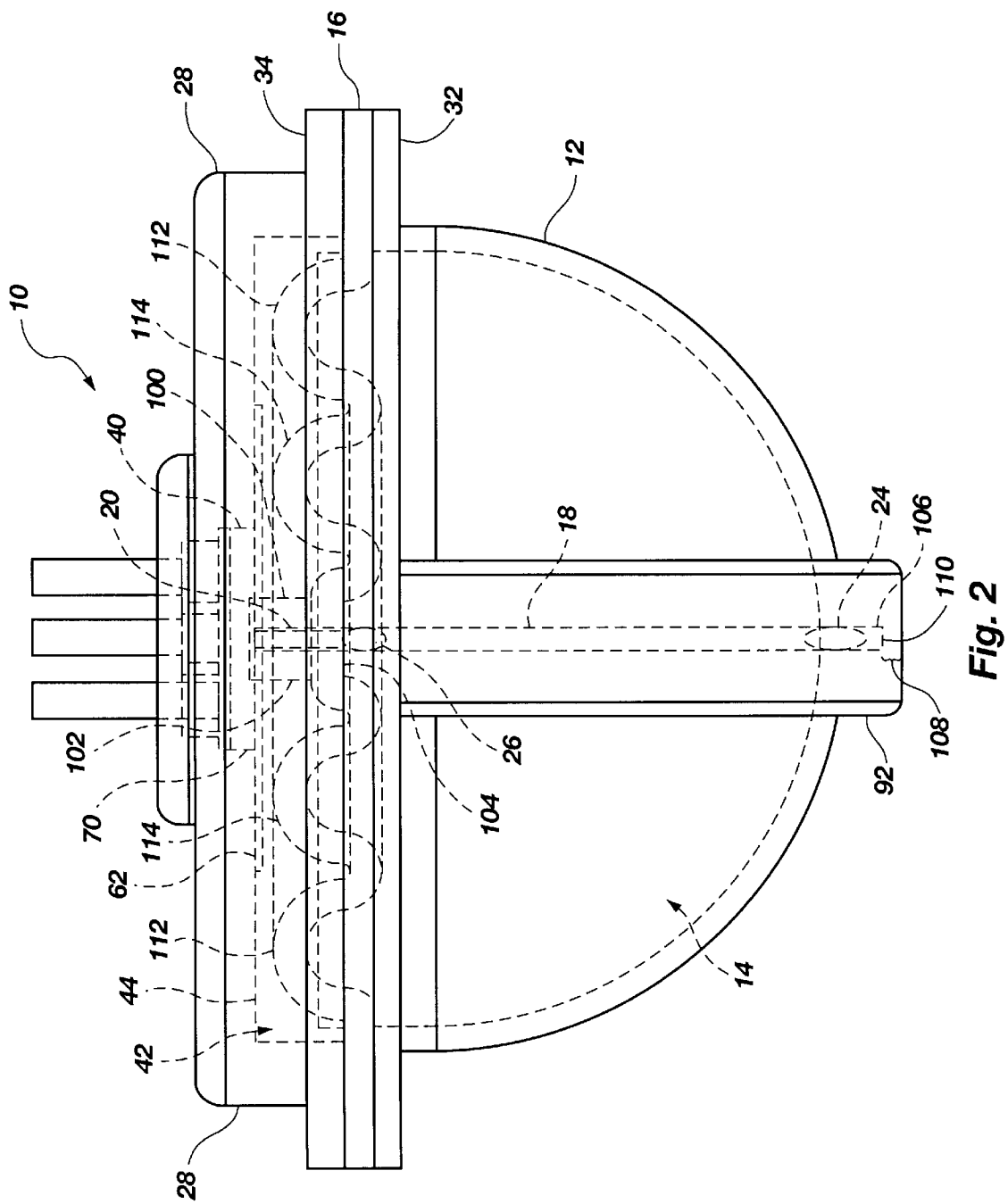
FIG. 2 is a side view of an assembled automatic injection device in accordance with the present invention.

Referring now to FIG. 2, a side view of the automatic injection device, generally indicated at 10, is shown as assembled. The membrane 16 is sandwiched between the flange 32 of the vessel 12 and the flange 34 of the end cap 28. Preferably, the flanges 32 and 34 and the membrane 16 are RF welded together or may be secured to one another with an epoxy or other adhesive known in the art. Similarly, structural members that clamp and hold the flanges 32 and 34 to the membrane could also be employed. Whatever the method employed to attach the components, a fluid tight seal must be maintained between the membrane 16 and the flange 32 even during pressurization of the chamber 42. The chamber 14 is substantially filled with a drug or other fluidic substance to be administered through the needle 16.

The needle 18 preferably is secured to the membrane 16 by a needle mount 100, comprising a substantially cylindrical structure having an internal bore 102 sized to substantially match the outer diameter of the needle 18. Preferably, the needle mount 100 is integrally formed into the membrane 16 and thus is formed from the same elastic and/or flexible material. As such, an interference fit between the bore 102 and the proximal end 20 of the needle may sufficiently hold the needle in position relative to the needle mount 100. An epoxy or some other adhesive known in the art could also be employed to secure the needle 18 relative to the needle mount 100. The opening 26 formed in the side of the needle is preferably positioned adjacent the lower surface 104 of the membrane 16 proximate the needle mount 100. The needle 18 extends from the needle mount 100 to the cap member 92. The cap member 92 is provided with an internal slot or recess 106 into which the sharp end 24 of the needle 18 resides prior to activation of the device 10. Thus, a thinned portion 108 is formed between the recess 106 and the outside surface 110 of the cap member 92.

In this embodiment, the membrane 16 is formed into one or more corrugations 112 and 114 that concentrically extend around the needle mount 100. These corrugations provide a means for the membrane 16 to expand into the interior chamber 14 of the vessel 12 when the propellant is ignited. It is also contemplated that the membrane 16 could be comprised of an elastic material that, when it forms a diaphragm over the chamber 14, has enough elasticity to stretch into the chamber 14. In addition, while two corrugations are illustrated, it is also contemplated that more or fewer corrugations could be employed in accordance with the present invention.

A second chamber 42 is formed between the membrane 16 and the interior surface 44 of the end cap 28. This second chamber becomes pressurized when the device 10 is activated thus forcing the membrane 16 into the chamber 14. The foil 62 is positioned between the needle mount 100 and the surface 44 and the propellant and igniter assembly 70 is positioned within the recess.

Figure 3:
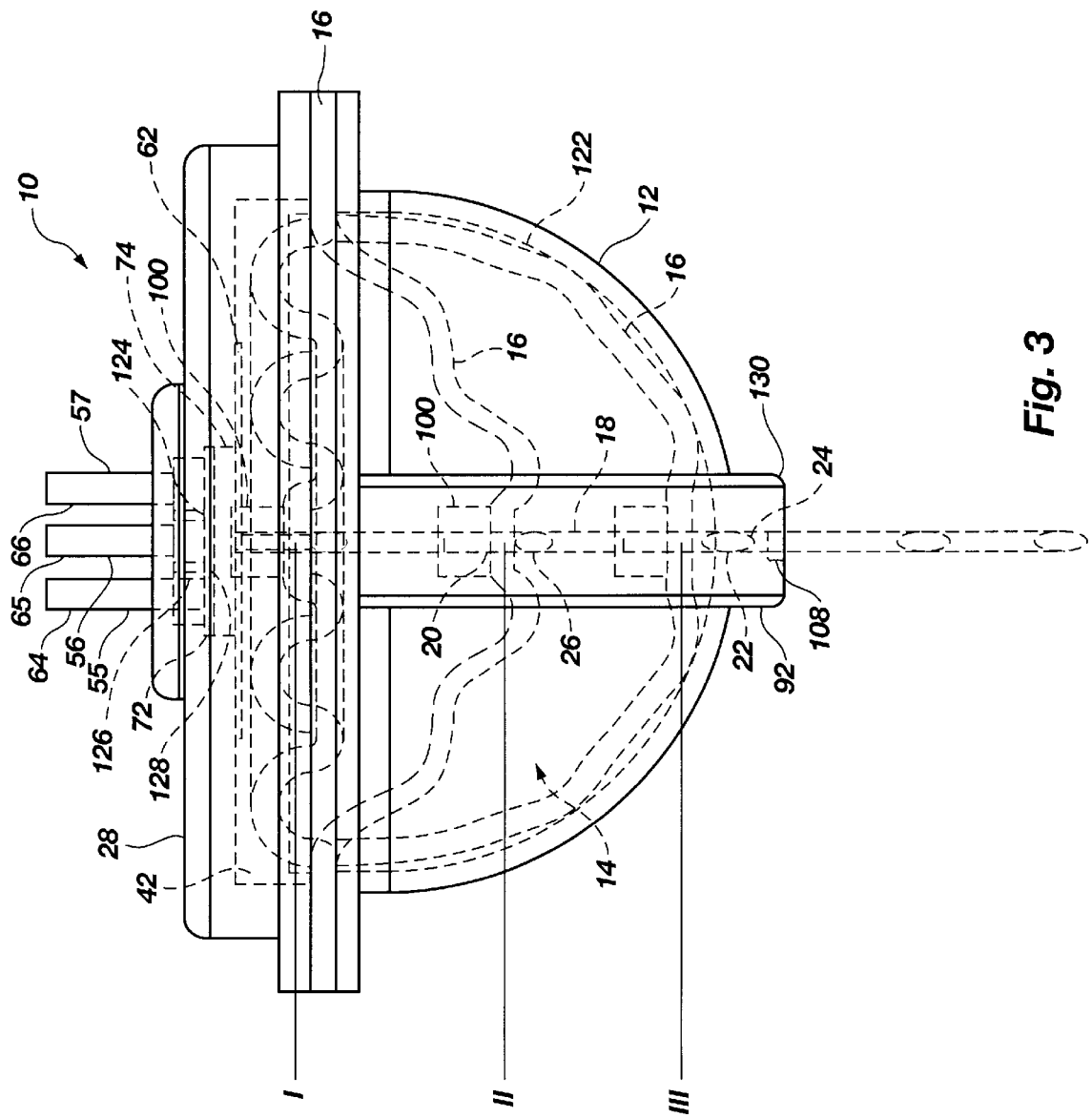
FIG. 3 is a side view of the assembled automatic injection device illustrated in FIG. 2 demonstrating a firing sequence of the automatic injection device.

FIG. 3 illustrates a firing sequence of the automatic injection device 10 illustrated in FIG. 2. In its natural or unstressed state, generally indicated at I, the membrane 16 generally lies in the same horizontal plane holding the needle 18 substantially perpendicular thereto. The tip 24 is thus held above the thinned portion 108 in the cap member 92 and may include a puncturable material such as polyurethane or some other material known in the art, or seal that at least is positioned proximate the tip 24 of the needle 18. A drug or other liquid substance to be delivered through the needle 18 substantially fills the chamber 14.

The shafts 64–66 of the connecting pins 55–57 extend above the end cap 28 for connection to a firing mechanism (not shown) which preferably provides an electrical current through at least two of the connecting pins 55–57 of sufficient amperage to heat a fusible link 124 present on the igniter 72 to a temperature at which the propellant 74 will ignite. For example, the fusible link 124 may comprise a 1 to 10 ohm resistor and the current source may have a voltage of approximately 1 to 6 volts but other voltages may be employed depending on the specific circuitry of the device. When the propellant ignites, the foil member 62 is forced toward the membrane 16, and the gases generated from the combustion process fill the chamber 42. The membrane 16 and thus the needle 18 is forced toward the distal end 130 of the vessel 12. The pressure of the gas within the chamber 14 thus forces the needle mount 100 toward the distal end 130 with enough force to cause the tip 24 of the needle to pierce the thinned portion 108 in the cap member 92. As indicated at II, the needle mount 100 and thus the needle 18 travel toward the distal end 130 as the needle protrudes through the cap member 92. As the needle 18 exits the cap member 92, it enters the skin of a patient to whom the injection is being administered. As such, the patients skin would be positioned adjacent to and in contact with the distal end 130 at the thinned portion 108 prior to activation of the injection device 10.

As the needle 18 travels through the vessel 12, the membrane 16 begins to unfold as the pressure within the second chamber 42 forces the membrane 16 into the first chamber 14. As the membrane 16 enters the chamber 14, the drug contained therein escapes through the opening 26 in the proximal end 20 of the needle 18 adjacent the needle mount 100. The drug thus flows through the hollow needle 18 and exits the opening 22 at the tip 24 of the needle.

As further illustrated, when the needle mount 100 reaches the position indicated at III, the needle 18 is substantially fully extended beyond the distal end 130 of the cap member 92, and the membrane 16 substantially matches the contour of the inner surface 122 of the vessel 12. Accordingly, substantially all of the drug is forced through the needle 18. While not illustrated as such, the membrane may be flexible enough that the pressure in the chamber 42 causes the membrane 16 to be pressed against substantially the entire surface 122 of the vessel 12 to effectively squeeze the drug out of the vessel 12 and through the needle 18.

Because of the added requirements of sharps handling procedures in the medical industry it is preferable that the needle 18 be retracted back into the vessel after the drug has been substantially evacuated therefrom. Thus, after a timed delay from the ignition of the propellant 74, a second electrical signal is sent through at least two of the connector pins 55–57 to a second fusible link 126 provided in communication with a hole 128 in the igniter 72. The hole 128 is preferably in communication with the hole 54 (shown in FIG. 1A). The vent or hole 128 is preferably filled with a meltable material, wax or polyurethane plug, that until melted provides a closed valve. In addition, such valves may also be mechanical, pressure actuated, or other valves known in the art. When the drug within the vessel 12 has been sufficiently evacuated therefrom, the second fusible link 126 is heated, causing the meltable material in the hole 128 to melt, and allowing the pressurized gasses in the chamber 42 to escape therethrough. As the gasses escape and the pressure within the chamber 42 drops, the membrane 16 acts as a spring, returning to its initial pre-firing position I, thus drawing the needle 18 back into the vessel 12. As such, the automatic injection device 10 is provided with a post-injection automatically retractable needle 18, thus eliminating the need for sharps handling of the automatic injection device 10.

It will be readily appreciated that the components of the present invention, as generally described and illustrated in the figures herein, could be arranged and designed in a wide variety of different configurations including modifications to and combinations of the preferred embodiments. For example, the automatic injection devices herein described need not be dome shaped, as other configurations, such as cylindrical, spherical, cubic, and the like, may also be possible. It is also contemplated that the automatic injection devices described herein may use other propellants to fire the device, such as a compressed liquid or gas or other materials known in the art. In addition, the injection devices may be used as individual, self contained units or they may be employed in single- or multi-injection devices that provide a source of electrical current and a handle for gripping by a user. In addition, it is to be understood that the above-described embodiments are only illustrative of the application of the principles of the present invention. Thus, numerous modifications and alternatives may be devised by those skilled in the art, including combinations of the various embodiments, without departing from the spirit and scope of the present invention.

Accordingly, the invention may be embodied in other specific forms without departing from its spirit or essential characteristics. The preferred embodiments are to be considered in all respects only as illustrative and not restrictive. The scope of the invention is, therefore, indicated by the appended claims, rather than by the foregoing description of the present embodiments. All changes which come within the meaning of the range of equivalency of the claims are to be embraced within their scope.

What is claimed is:

1. An apparatus for delivering a drug, comprising:
    a housing defining a first opening at a proximal end thereof, having a distal end, and having an inner surface defining a chamber;
    a puncturable seal secured to the distal end of said housing;
    a resilient membrane having a first side and a second side and disposed within said chamber, said resilient membrane and said housing defining a drug reservoir between said first side of said resilient membrane and said inner surface and defining a pressure chamber between said second side of said resilient membrane and said inner surface;
    a hollow needle having a distal end and a proximal end secured to said resilient membrane proximate said proximal end of said hollow needle and positioned with said distal end proximate said puncturable seal, having a first opening at said distal end, and a second opening in a side thereof proximate said proximal end; and
    a pressure source in communication with said pressure chamber.

2. The apparatus of claim 1, wherein said housing is comprised of a drug containment portion secured relative to said first side of said resilient member and a cap portion secured relative to said second side of said resilient member.

3. The apparatus of claim 2, wherein said drug containment portion has a dome-like shape.

4. The apparatus of claim 3, wherein said hollow needle is secured to a mid-portion of said resilient member and said distal end of said hollow needle is positioned proximate a center of said dome-like shaped drug containment portion.

5. The apparatus of claim 1, wherein said housing is comprised of polyurethane.

6. The apparatus of claim 1, wherein said resilient member comprises an expandable structure.

7. The apparatus of claim 6, wherein said expandable structure is configured with a plurality of corrugations.

8. The apparatus of claim 7, wherein said plurality of corrugations are concentrically configured.

9. The apparatus of claim 1, wherein said resilient member is comprised of at least one of silicone, latex, rubber, and polyurethane.

10. The apparatus of claim 1, wherein said puncturable seal forms a seal at said distal end of said housing.

11. The apparatus of claim 10, wherein said puncturable seal is comprised of polyurethane.

12. The apparatus of claim 1, wherein said pressure source comprises a combustible propellant and an igniter in communication with said propellant.

13. The apparatus of claim 12, wherein said igniter comprises an electrical circuit including a first fusible link disposed adjacent said propellant for igniting said propellant.

14. The apparatus of claim 13, further comprising a second fusible link in communication with a vent defined in said housing and further including a meltable material disposed within said vent and in communication with said second fusible link.

15. The apparatus of claim 13, wherein said first fusible link comprises a resistor.

16. The apparatus of claim 1, wherein said hollow needle is comprised of stainless steel.

17. A drug delivery apparatus, comprising:
   (a) vessel means for containing a drug therein;
   (b) flexible expulsion means for expelling the drug from the vessel means, said flexible expulsion means is a diaphragm that is concentrically corrugated;
   (c) forcing means for forcing the flexible expulsion means at least partially into said vessel means; and
   (d) ejection means in fluid communication with said vessel means for delivering the drug from the vessel means.

18. The apparatus of claim 17, wherein said vessel means comprises a substantially rigid container.

19. The apparatus of claim 17, wherein said forcing means comprises a pressure source.

20. The apparatus of claim 19, wherein said pressure source comprises a propellant and an ignition source in communication with said propellant.

21. The apparatus of claim 19, wherein said pressure source comprises a compressed gas.

22. The apparatus of claim 17, wherein said ejection means comprises a hollow needle.

23. The apparatus of claim 22, further comprising a puncturable seal and said hollow needle includes a sharp end, said puncturable seal positioned on a wall of said vessel means proximate said sharp end of said hollow needle.

24. The apparatus of claim 17, wherein said flexible expulsion means forms a seal at an open end of said vessel means.

25. A drug delivery apparatus, comprising:
   (a) a vessel, containing a drug therein;
   (b) a diaphragm, having a concentrically corrugated shape, positioned to expel the drug from the vessel;
   (c) a forcing device that biases the diaphragm at least partially into said vessel; and
   (d) a hollow needle, coupled to the vessel to allow the drug to be expelled therefrom, having:
      i) a first opening at a proximal end thereof that is secured to said diaphragm; and
      ii) a second opening proximate the distal end and positioned within said vessel.

26. The apparatus of claim 25, wherein the forcing device comprises a pressure source.

27. The apparatus of claim 26, wherein the pressure source comprises a propellant and an ignition source in communication with the propellant.

28. The apparatus of claim 26, wherein the pressure source comprises a compressed gas.

* * * * *